United States Patent
Li et al.

(10) Patent No.: US 11,375,721 B1
(45) Date of Patent: Jul. 5, 2022

(54) MOSQUITO REPELLENT COMPOSITION, PREPARATION METHOD AND APPLICATION THEREOF

(71) Applicant: LOOBI (GUANGZHOU) HEALTH INDUSTRY CO., LTD, Guangdong (CN)

(72) Inventors: Yichun Li, Guangdong (CN); Jingyan Yang, Guangdong (CN)

(73) Assignees: LOOBI (GUANGZHOU) HEALTH INDUSTRY CO., LTD, Guangdong (CN); GUANGDONG LOOBI HEALTH TECHNOLOGY CO., LTD., Guangdong (CN)

( * ) Notice: Subject to any disclaimer, the term of this patent is extended or adjusted under 35 U.S.C. 154(b) by 0 days.

(21) Appl. No.: 17/401,426

(22) Filed: Aug. 13, 2021

(51) Int. Cl.
| | |
|---|---|
| *A01N 65/22* | (2009.01) |
| *A01N 25/04* | (2006.01) |
| *A01N 25/22* | (2006.01) |
| *A01N 65/26* | (2009.01) |
| *A01N 65/36* | (2009.01) |
| *A01N 25/30* | (2006.01) |
| *A01N 65/08* | (2009.01) |
| *A01N 25/08* | (2006.01) |
| *A01P 17/00* | (2006.01) |

(52) U.S. Cl.
CPC ............. *A01N 65/22* (2013.01); *A01N 25/04* (2013.01); *A01N 25/08* (2013.01); *A01N 25/22* (2013.01); *A01N 25/30* (2013.01); *A01N 65/08* (2013.01); *A01N 65/26* (2013.01); *A01N 65/36* (2013.01); *A01P 17/00* (2021.08)

(58) Field of Classification Search
None
See application file for complete search history.

(56) References Cited

U.S. PATENT DOCUMENTS

2014/0335140 A1* 11/2014 Hoag .................... A61K 36/53
424/412

FOREIGN PATENT DOCUMENTS

| CN | 104042497 A | 9/2014 |
| CN | 107468561 A | 12/2017 |
| CN | 109223664 A | 1/2019 |
| CN | 111773140 A | 10/2020 |
| KR | 20150021780 A | 3/2015 |

OTHER PUBLICATIONS

Ferreria, M.R.A. et al., "Development and evaluation of emulsions from Carapa guianensis (Andiroba) oil," AAPS PharmSciTech, vol. 11(3), pp. 1382-1390 (2010).*
Miot, H.A. et al., "Comparison among homemade repellents made with cloves, picaridin, andiroba, and soybean oil against Aedes aegypti bites," Revista da Sociedade Brasileira de Medicina Tropical, vol. 44(6), pp. 793-794 (2011).*
Watanabe, K. et al., "Rotundial, a new natural mosquito repellent from the leaves of Vitex rotundifolia," Bioscience, Biotechnology, and Biochemistry, vol. 59(10), pp. 1979-1980 (1995).*
CN Search report dated Aug. 10, 2021 in Chinese application (No. 202011555427X).
English translation of CN Search report dated Aug. 10, 2021 in Chinese application (No. 202011555427X).
English translation of CN Office Action dated May 28, 2021 in Chinese application (No. 202011555427X).

\* cited by examiner

*Primary Examiner* — John Pak
(74) *Attorney, Agent, or Firm* — McClure, Qualey & Rodack, LLP

(57) ABSTRACT

The present invention belongs to mosquito repellent technical field, and specifically a mosquito repellent composition, preparation method and application thereof. The mosquito repellent composition comprises following ingredients and mass fractions thereof: composite plant oil 7-10 parts, gromwell root extracts 3-5 parts, *Vitex rotundifolia* extracts 1-3 parts, sustained release agents 1-2 parts, emulsifying agents 2-4 parts, stabilizing agents 0.1-0.3 part, and water 165-182 parts. The mosquito repellent composition provided in the present invention doesn't contain chemical ingredients such as DEET and methothrin etc., and works in combination with natural plant essence oil, which is highly safe, free from irritation, allergic reactions and other side effects, and can be used to repel mosquitoes safely, gently and is suitable for long term use.

8 Claims, No Drawings

MOSQUITO REPELLENT COMPOSITION, PREPARATION METHOD AND APPLICATION THEREOF

TECHNICAL FIELD

The present invention belongs to a mosquito repellent technical field, and specifically relates to a mosquito repellent composition, preparation method and application thereof.

BACKGROUND TECHNOLOGY

Mosquitoes spread a variety of mosquito-borne diseases, which endanger human health, such as malaria, yellow fever, dengue fever, Western equine encephalitis, Japanese encephalitis, West Nile virus disease, etc. At present, there are about 3,500 mosquitoes and their subtypes in the world. Species of the most common mosquitoes are *Aedes, Culex* and *Anopheles*. People are constantly developing and researching on corresponding mosquito repellent products. Mosquito coils are the oldest natural medicine to repel mosquitoes. As early as the Southern Song Dynasty, mosquito repellent incense sticks made of Chinese medicine appeared. The effective ingredient in modern mosquito coils is pyrethrin, which is effective in repelling mosquitoes. After the mosquito coil is ignited, the pyrethrin in the mosquito coil volatilizes along with the smoke and spreads in the indoor air, paralyzing the mosquito's nerves, so the mosquitoes fall to the ground and die, or run away, thereby repelling the mosquitoes. The mosquito repellent effect of electric mosquito incense is also good, generally lasting 6-8 hours. The mosquito repellent principle of electric mosquito coils is to inhale pyrethrum and other mosquito repelling ingredients into the mosquito mats, and evaporate the same after heating. Liquid electric mosquito coils utilize capillary principle to continuously heat and release insecticide substances. But both electric mosquito coils and liquid electric mosquito coils contain organic compounds that are harmful to the human body. If used in a confined room, adverse reactions may occur. The main component of the anti-mosquito liquid is diethyltoluamide (DEET), and principle thereof is to directly act on the tactile organs and chemoreceptors of mosquitoes to drive away mosquitoes. In addition, if one has been bitten by mosquitoes, the existing mosquito repellent products on the market have poor anti-itching effects.

At present, most of mosquito repellent products commercially available contain chemical ingredients such as DEET and methothrin etc., and upon long term use adverse effects may be done to human health and for products containing natural plant compositions currently available, mosquito repellent durations of are short, itching relieving effects poor, and functions are quite single.

SUMMARY OF THE INVENTION

Targeting at deficiencies of the prior art, a purpose of the present invention is to provide a mosquito repellent composition, preparation method and application thereof. The mosquito repellent composition provided in the present invention doesn't contain chemical ingredients such as DEET and methothrin etc., and works in combination with natural plant essence oil, which is highly safe, free from irritation, allergic reactions and other side effects, and can be used to repel mosquitoes safely, gently and is suitable for long term use. Furthermore, the mosquito repellent composition provided in the present invention provides a good mosquito repelling effect, a long mosquito repelling time, and obvious antipruritic effects after mosquito bites.

A mosquito repellent composition, comprises following ingredients and mass fractions thereof:

Composite plant oil 7-10 parts, gromwell root extracts 3-5 parts, *Vitex rotundifolia* extracts 1-3 parts, sustained release agents 1-2 parts, emulsifying agents 2-4 parts, stabilizing agents 0.1-0.3 part, and water 165-182 parts. Further, the mosquito repellent composition comprises following ingredients and mass fractions thereof:

Composite plant oil 9 parts, gromwell root extracts 4 parts, *Vitex rotundifolia* extracts 2 parts, sustained release agents 1.5 parts, emulsifying agents 3 parts, stabilizing agents 0.2 part, and water 175 parts.

Further, the composite plant oil is made from *Carapa guianensis* seed oil and bergamot orange oil at a mass ratio of 4-6:3-5.

Further, the composite plant oil is made from *Carapa guianensis* seed oil and bergamot orange oil at a mass ratio of 5:4.

Further, a preparation method of the gromwell root extracts is:

(1) Grinding gromwell roots, filtering with a 50-80-mesh filter, and getting coarse gromwell root powder;

(2) Freezing processing the coarse gromwell root powder obtained in step (1) at a freezing temperature of 0-4° C. for 4-6 h and getting frozen coarse gromwell root powder;

(3) Grinding the frozen coarse gromwell root powder obtained in step (2), filtering with a 100-150-mesh filter and getting fine gromwell root powder; and (4) Putting the fine gromwell root powder obtained in step (3) to a container, adding ethanol water solution with a mass of 8-15 times of a mass of the fine gromwell root powder, extraction by ultrasonic extraction at an ultrasonic power of 100-200 W for 7-12 min, and filtering until no ethanol flavor is perceived, and obtaining the gromwell root extracts.

Further, the sustained release agents are made from nano-meter attapulgite, polyvinyl alcohol and chitosan oligosaccharide at a mass ratio of 1-2:5-7:12-15.

Further still, the sustained release agents are made from nano-meter attapulgite, polyvinyl alcohol and chitosan oligosaccharide at a mass ratio of 2:6:13.

Further, a grain size of the nano-meter attapulgite is 10-30 nm.

Further still, a grain size of the nano-meter attapulgite is 20 nm.

Still further, the emulsifying agents are made from alkyl glycoside and cetearyl glucoside at a mass ratio of 2-3:5-8.

Still further, the emulsifying agents are made from alkyl glycoside and cetearyl glucoside at a mass ratio of 3:7.

Another purpose of the present invention is to provide a preparation method of the mosquito repelling composition, in following steps:

S1: mixing the composite plant oil and the emulsifying agents, stirring evenly and getting a mixture A;

S2: adding water into the stabilizing agents, stirring until fully dissolved, adding the sustained release agents, stirring evenly and getting a mixture B; and S3: at a mixing rate of 200 r/min, adding the mixture A obtained in step S1 to the mixture B obtained in step S2, stirring for 30 min, adding the gromwell root extracts and the *Vitex rotundifolia* extracts, continuing stirring for 30 min, and the mosquito repellent composition can be got.

Another purpose of the present invention is to provide an application of the mosquito repellent composition in making mosquito repellent products with mosquito repellent and/or itching relieving effects.

The mosquito repellent composition comprising composite plant oil, gromwell root extracts, *Vitex rotundifolia* extracts, sustained release agents, emulsifying agents and stabilizing agents etc., without containing chemical ingredients such as DEET and methothrin, is highly safe, free from irritation, allergic reactions and other side effects, and can be used to repel mosquitoes gently and safely, while effectively and for a long time, and in the meantime, good itching relieving effects can be achieved. The sustained release agents made from nano-meter attapulgite, polyvinyl alcohol and chitosan oligosaccharide at a predetermined mass ratio can control a volatilization rate of the composite plant oil, so that the product can play a mosquito repellent role for a longer time. By a process of grinding the gromwell root to be coarse gromwell root powder, freezing processing the coarse gromwell root powder and grinding the frozen coarse gromwell root powder, active ingredients of gromwell root can be dissolved out effectively during ultrasonic extraction and itching relieving and antioncotic effects of the gromwell root extracts can be improved.

In the present invention, the gromwell root is a root of comfrey, *Macrotomia euchroma* or *Onosma paniculatum* of comfrey genus.

Compared with the prior art, the present invention has following advantages:
(1) With the mosquito repellent composition prepared according to the present invention, harmful substances on the skin can be inhibited effectively and quick antipruritic effects can be achieved after mosquito bites.
(2) The mosquito repellent composition provided in the present invention doesn't contain chemical ingredients such as DEET and methothrin etc., and works in combination with natural plant essence oil, which is highly safe, free from irritation, allergic reactions and other side effects, and can be used to repel mosquitoes safely, gently and is suitable for long term use.

EMBODIMENTS

The present invention will be further explained through description of specific embodiments below, but the following description is not a limitation of the present invention. Those skilled in the art can make a variety of modifications and improvements according to basic ideas of the present invention; however, as long as these modifications and improvements don't depart from the basic ideas of the present invention, they fall into protection scope of the present invention.

In case not specified otherwise, raw materials used in the present invention are commercially available ones. For example, the *Carapa guianensis* seed oil is bought from Guangzhou C-now Biotech Co., Ltd. with a product description of Jarxotic™ AN20 *Carapa guianensis* seed oil, brand name: Jarchem; bergamot orange oil can be bought from Shenzhen Dingcheng Plant Perfume Co., Ltd., with an article no. of DC-23; the *Vitex rotundifolia* extract can be bought from Xi'an Orient Biotechnology Co., Ltd; the polyvinyl alcohol can be bought from Guangzhou Hualisen Trade Co., Ltd with an article no. of PVA420H; the chitosan oligosaccharide can be bought from Shanxi Lvlai Biotech Co., Ltd. with an article no. of LL732; the alkyl glycoside can be bought from Guangzhou Riyou Technology Co., Ltd. with a model of APG08-14; the cetearyl glucoside can be bought from Beijing Baiao Laibo Technology Co., Ltd., with an article no. of Y15177 and the carbomer 940 can be bought from Guangzhou Bofeng Biotechnology Co., Ltd. with a model no. of 940.

Embodiment 1 Mosquito Repellent Composition

The mosquito repellent composition comprises the following ingredients and mass percentages thereof are as following:
Composite plant oil 7 parts, gromwell root extracts 3 parts, *Vitex rotundifolia* extracts 1 parts, sustained release agents 1 parts, emulsifying agents 2 parts, stabilizing agents 0.1 part, and water 165 parts; the composite plant oil is made from *Carapa guianensis* seed oil and bergamot orange oil at a mass ratio of 4:5; the sustained release agents are made from nano-meter attapulgite, polyvinyl alcohol and chitosan oligosaccharide with a grain size of 10 nm at a mass ratio of 1:7:15; the emulsifying agents are made from alkyl glycoside and cetearyl glucoside at a mass ratio of 2:8; and the stabilizing agents are carbomer 940.

Further, a preparation method of the gromwell root extracts is:
(1) Grinding gromwell roots, filtering with a 50-mesh filter, and getting coarse gromwell root powder;
(2) Freezing processing the coarse gromwell root powder obtained in step (1) at a freezing temperature of 0° C. for 4 h and getting frozen coarse gromwell root powder;
(3) Grinding the frozen coarse gromwell root powder obtained in step (2), filtering with a 100-mesh filter and getting fine gromwell root powder; and
(4) Putting the fine gromwell root powder obtained in step (3) to a container, adding ethanol water solution with a volume fraction of 95% with a mass of 8 times of a mass of the fine gromwell root powder, ultrasonic extracting with an ultrasonic power of 100 W for 7 min, filtering, filtrate decompression and condensation until no ethanol flavor can be perceived, and getting the gromwell root extracts.

A preparation method of the foregoing mosquito repelling composition, in following steps:
S1: mixing the composite plant oil and the emulsifying agents, stirring evenly and getting a mixture A;
S2: adding water into the stabilizing agents, stirring until fully dissolved, adding the sustained release agents, stirring evenly and getting a mixture B; and
S3: at a mixing rate of 200 r/min, adding the mixture A obtained in step S1 to the mixture B obtained in step S2, stirring for 30 min, adding the gromwell root extracts and the *Vitex rotundifolia* extracts, continuing stirring for 30 min, and the mosquito repellent composition can be got.

Embodiment 2 Mosquito Repellent Composition

The mosquito repellent composition comprises the following ingredients and mass percentages thereof are as following:
Composite plant oil 10 parts, gromwell root extracts 5 parts, *Vitex rotundifolia* extracts 3 parts, sustained release agents 2 parts, emulsifying agents 4 parts, stabilizing agents 0.3 part, and water 182 parts; the composite plant oil is made from *Carapa guianensis* seed oil and bergamot orange oil at a mass ratio of 6:3; the sustained release agents are made from nano-meter attapulgite, polyvinyl alcohol and chitosan oligosaccharide with a grain size of 30 nm at a mass ratio of 2:5:12; the emulsifying agents are made from alkyl glycoside and cetearyl glucoside at a mass ratio of 3:5; and the stabilizing agents are carbomer 940.

Further, a preparation method of the gromwell root extracts is:
(5) Grinding gromwell roots, filtering with a 80-mesh filter, and getting coarse gromwell root powder;
(6) Freezing processing the coarse gromwell root powder obtained in step (1) at a freezing temperature of 4° C. for 6 h and getting frozen coarse gromwell root powder;
(7) Grinding the frozen coarse gromwell root powder obtained in step (2), filtering with a 150-mesh filter and getting fine gromwell root powder; and
(8) Putting the fine gromwell root powder obtained in step (3) to a container, adding ethanol water solution with a volume fraction of 95% with a mass of 15 times of a mass of the fine gromwell root powder, ultrasonic extracting with an ultrasonic power of 200 W for 12 min, filtering, filtrate decompression and condensation until no ethanol flavor can be perceived, and getting the gromwell root extracts.

A preparation method of the foregoing mosquito repellent composition is similar to the preparation method used in embodiment 1.

Embodiment 3 Mosquito Repellent Composition

The mosquito repellent composition comprises the following ingredients and mass percentages thereof are as following:

Composite plant oil 9 parts, gromwell root extracts 4 parts, *Vitex rotundifolia* extracts 2 parts, sustained release agents 1.5 parts, emulsifying agents 3 parts, stabilizing agents 0.2 part, and water 175 parts; the composite plant oil is made from *Carapa guianensis* seed oil and bergamot orange oil at a mass ratio of 5:4; the sustained release agents are made from nano-meter attapulgite, polyvinyl alcohol and chitosan oligosaccharide with a grain size of 20 nm at a mass ratio of 2:6:13; the emulsifying agents are made from alkyl glycoside and cetearyl glucoside at a mass ratio of 3:7; and the stabilizing agents are carbomer 940.

Further, a preparation method of the gromwell root extracts is:
(1) Grinding gromwell roots, filtering with a 60-mesh filter, and getting coarse gromwell root powder;
(2) Freezing processing the coarse gromwell root powder obtained in step (1) at a freezing temperature of 2° C. for 5 h and getting frozen coarse gromwell root powder;
(3) Grinding the frozen coarse gromwell root powder obtained in step (2), filtering with a 120-mesh filter and getting fine gromwell root powder; and
(4) Putting the fine gromwell root powder obtained in step (3) to a container, adding ethanol water solution with a volume fraction of 95% with a mass of 9 times of a mass of the fine gromwell root powder, ultrasonic extracting with an ultrasonic power of 120 W for 9 min, filtering, filtrate decompression and condensation until no ethanol flavor can be perceived, and getting the gromwell root extracts.

A preparation method of the foregoing mosquito repellent composition is similar to the preparation method used in embodiment 1.

Comparative Example 1 Mosquito Repellent Composition

The mosquito repellent composition comprises the following ingredients and mass percentages thereof are as following:

Composite plant oil 9 parts, gromwell root extracts 4 parts, *Vitex rotundifolia* extracts 2 parts, sustained release agents 1.5 parts, emulsifying agents 3 parts, stabilizing agents 0.2 part, and water 175 parts; the composite plant oil is made from *Carapa guianensis* seed oil and bergamot orange oil at a mass ratio of 5:4; the sustained release agents are made from polyvinyl alcohol and chitosan oligosaccharide at a mass ratio of 6:13; the emulsifying agents are made from alkyl glycoside and cetearyl glucoside at a mass ratio of 3:7; and the stabilizing agents are carbomer 940.

The preparation method of the gromwell root extracts is similar to the preparation method of the gromwell root extracts in embodiment 3.

The preparation method of the mosquito repellent composition is similar to the preparation method of the mosquito repellent composition in embodiment 1.

What is different with embodiment 3 is that the sustained release agents are made from polyvinyl alcohol and chitosan oligosaccharide at a mass ratio of 6:13.

Comparative Example 2 Mosquito Repellent Composition

The mosquito repellent composition comprises the following ingredients and mass percentages thereof are as following:

Composite plant oil 9 parts, gromwell root extracts 4 parts, *Vitex rotundifolia* extracts 2 parts, sustained release agents 1.5 parts, emulsifying agents 3 parts, stabilizing agents 0.2 part, and water 175 parts; the composite plant oil is made from *Carapa guianensis* seed oil and bergamot orange oil at a mass ratio of 5:4; the sustained release agents are made from nano-meter attapulgite, polyvinyl alcohol and chitosan oligosaccharide with a grain size of 20 nm at a mass ratio of 2:6:13; the emulsifying agents are made from alkyl glycoside and cetearyl glucoside at a mass ratio of 3:7; and the stabilizing agents are carbomer 940.

Further, a preparation method of the gromwell root extracts is:
(1) Grinding gromwell roots, filtering with a 120-mesh filter, and getting fine gromwell root powder;
(2) Putting the fine gromwell root powder obtained in step (1) to a container, adding ethanol water solution with a volume fraction of 95% with a mass of 9 times of a mass of the fine gromwell root powder, ultrasonic extracting with an ultrasonic power of 120 W for 9 min, filtering, filtrate decompression and condensation until no ethanol flavor can be perceived, and getting the gromwell root extracts.

The preparation method of the mosquito repellent composition is similar to the preparation method of the mosquito repellent composition in embodiment 1.

Experiment 1 Quality Test

1. Test materials: the mosquito repellent compositions obtained in embodiment 1, embodiment 2 and embodiment 3.
2. Test method:
Test multiple screen items of the products in accordance with corresponding screening methods in Method II of Part II of Chinese Agricultural Industry Standard NY/T 761-2008.
3. Experiment results: the experimental results are shown in table 1

TABLE 1

| Screening items | unit | Embodiment 1 | Embodiment 2 | Embodiment 3 |
|---|---|---|---|---|
| Cypermethrin and beta-cypermethrin | mg/kg | Not detected | Not detected | Not detected |
| Cyhalothrin and lambda-cyhalothrin | mg/kg | Not detected | Not detected | Not detected |
| Cyhalothrion and beta-cyfluthrin | mg/kg | Not detected | Not detected | Not detected |
| Sumicidin and Esfenvalerate | mg/kg | Not detected | Not detected | Not detected |
| Permethrin | mg/kg | Not detected | Not detected | Not detected |
| Deltamethrin | mg/kg | Not detected | Not detected | Not detected |
| Bifenthrin | mg/kg | Not detected | Not detected | Not detected |
| Fenpropathrin | mg/kg | Not detected | Not detected | Not detected |

As can be seen in table 1, chemical ingredients such as cypermethrin and beta-cypermethrin, cyhalothrin and lambda-cyhalothrin etc, have not been detected in the mosquito repellent composition in the present invention, and safety of the mosquito repellent composition according to the present invention is high.

Experiment 2 Mosquito Repellent Effect Test

1. Test materials: the mosquito repellent compositions obtained in embodiment 3 and comparative example 1.
2. Test method:

Mosquito repellent effect tests are done based on Chinese Standard GB/T13917.9-2009 *Health insecticides for pesticide registration and evaluation of laboratory efficacy test—Part 9: Repellent*. Species of tested mosquitoes: female adults of *Aedes albopictus* that have not sucked blood for 3-5 days after eclosion emergence.

3. Experiment results: the experimental results are shown in table 2 and the evaluation standards are shown in table 3.

TABLE 2 mosquito repellent test results

| Test items | Embodiment 3 | Comparative example 1 |
|---|---|---|
| Effective protection time (h) | 8.5 | 7.0 |

TABLE 3 evaluation references

| Effective protection time | Class |
|---|---|
| ≥6.0 h | A |
| ≥4.0 h | B |

As can be seen in table 2 and table 3, the mosquito repellent composition prepared in embodiment 3 has good mosquito repellent effects, and effective protection time of the mosquito repellent composition for the testers is as long as 8.5 h with a test class A. wherefrom, the mosquito repellent composition according to the present invention can be used to repel mosquitoes for a long time and effectively.

Experiment 3 Antipruritic and Antioncotic Effect Test

1. Test materials: the mosquito repellent compositions obtained in embodiment 3 and comparative example 2.
2. Test method: choose 40 volunteers, 20 of whom are male and another 20 are female, sitting quietly beside green belts in a community, choose among volunteers with itching and swellings on the arms caused by mosquito bites those with two or more swellings which are quite obvious (diameters of the swellings bigger than 1.5 cm) to conduct itching relieving and antioncotic effect test, applying in one swelling the mosquito repellent composition prepared in embodiment 3 and in another swelling the mosquito repellent composition prepared in comparative example 2. Give rates of effective itching relieving time, effective itching relieving duration and antioncotic effects by the volunteers.
3. Test results: the evaluation standards are shown in table 4 and the test results are shown in table 5.

TABLE 4 evaluation standards

| Evaluation items | Evaluation standards | | | |
|---|---|---|---|---|
| | 3 | 2 | 1 | 0 |
| Effective itching relieving time | Itching relieving immediately | Itching relieving within 1 minute | Itching relieving within 3 minutes | Not effective |
| Effective itching relieving duration | Itching relieving duration >2 h | Itching relieving time between 1 h and 2 h | Itching relieving time between 0.5 h to 1 h | Itching relieving time <0.5 h |
| Antioncotic effects | The swellings subside significantly in 24 h after application (reduction of diameters of swellings >50%) | The swellings subside to some extent in 24 h after application (reduction of diameters of swellings between 25~50%) | The swellings subside slightly in 24 h after application (reduction of diameters of swellings between 10~25%) | No change happens in 24 h after application (reduction of diameters of swellings less than 10%) |

TABLE 5 itching relieving and antioncotic effect test results

| Evaluation results | Embodiment 3 | Comparative example 1 |
|---|---|---|
| Effective itching relieving time | 2.8 | 2.3 |
| Effective itching relieving duration | 2.9 | 2.4 |
| Antioncotic effects | 3.0 | 2.5 |

As can be seen in table 5, the effective itching relieving time, the effective itching relieving duration and the antioncotic effects of the mosquito repellent composition prepared according to embodiment 3 of the present invention have high rates, which establishes that, the mosquito repellent composition according to the present invention can be used to relieve itching rapidly, and has good antioncotic effects. Compared with comparative example 2, itching relieving and antioncotic effects of the mosquito repellent composition according to the present invention are better. And the testers said that, the mosquito repellent composition according to the present invention is gentle and non-irritating.

The invention claimed is:

1. A mosquito repellent composition, comprising the following ingredients and mass fractions thereof:
   composite plant oil 7-10 parts, gromwell root extracts 3-5 parts, *Vitex rotundifolia* extracts 1-3 parts, sustained release agents 1-2 parts, emulsifying agents 2-4 parts, stabilizing agent 0.1-0.3 part, and water 165-182 parts;
   wherein the composite plant oil is made from *Carapa guianensis* seed oil and bergamot orange oil at a mass ratio of 4-6:3-5;
   wherein the sustained release agents are made from nano-meter attapulgite, polyvinyl alcohol and chitosan oligosaccharide at a mass ratio of 1-2:5-7:12-15;
   wherein the emulsifying agents are made from alkyl glycoside and cetearyl glucoside at a mass ratio of 2-3:5-8;
   wherein the stabilizing agent is carbomer 940;
   wherein a preparation method of the gromwell root extracts is:
   (1) grinding gromwell roots, filtering with a 50-80-mesh filter, and obtaining coarse gromwell root powder;
   (2) chilling the coarse gromwell root powder obtained in step (1) at a chilling temperature of 0-4° C. for 4-6 h and obtaining chilled coarse gromwell root powder;
   (3) grinding the chilled coarse gromwell root powder obtained in step (2), filtering with a 100-150-mesh filter and obtaining fine gromwell root powder;
   (4) putting the fine gromwell root powder obtained in step (3) in a container,
   (5) adding ethanol water solution with a mass of the ethanol water solution 8-15 times the mass of the fine gromwell root powder, and extracting by ultrasonic extraction at an ultrasonic power of 100-200 W for 7-12 min,
   (6) filtering until no ethanol flavor is perceived, and
   (7) obtaining the gromwell root extracts.

2. The mosquito repellent composition according to claim 1, further comprising following ingredients and mass fractions thereof:
   composite plant oil 9 parts, gromwell root extracts 4 parts, *Vitex rotundifolia* extracts 2 parts, sustained release agents 1.5 parts, emulsifying agents 3 parts, stabilizing agent 0.2 part, and water 175 parts.

3. The mosquito repellent composition according to claim 1, wherein a grain size of the nano-meter attapulgite is 10-30 nm.

4. The mosquito repellent composition according to claim 1, wherein a grain size of the nano-meter attapulgite is 20 nm.

5. A preparation method of the mosquito repelling composition according to claim 1, comprising following steps:
   S1: mixing the composite plant oil and the emulsifying agents, stirring evenly and obtaining a mixture A;
   S2: adding water into the stabilizing agent, stirring until fully dissolved, adding the sustained release agents, stirring evenly and obtaining a mixture B; and
   S3: at a mixing rate of 200 r/min, adding the mixture A obtained in step S1 to the mixture B obtained in step S2, stirring for 30 min, adding the gromwell root extracts and the *Vitex rotundifolia* extracts, continuing stirring for 30 min, and obtaining the mosquito repellent composition.

6. The mosquito repellent composition according to claim 2, wherein a grain size of the nano-meter attapulgite is 10-30 nm.

7. The mosquito repellent composition according to claim 2, wherein a grain size of the nano-meter attapulgite is 20 nm.

8. A preparation method of the mosquito repelling composition according to claim 2, comprising following steps:
   S1: mixing the composite plant oil and the emulsifying agents, stirring evenly and obtaining a mixture A;
   S2: adding water into the stabilizing agent, stirring until fully dissolved, adding the sustained release agents, stirring evenly and obtaining a mixture B; and
   S3: at a mixing rate of 200 r/min, adding the mixture A obtained in step S1 to the mixture B obtained in step S2, stirring for 30 min, adding the gromwell root extracts and the *Vitex rotundifolia* extracts, continuing stirring for 30 min, and obtaining the mosquito repellent composition.

* * * * *